United States Patent [19]
de Fraine et al.

[11] Patent Number: 5,439,910
[45] Date of Patent: Aug. 8, 1995

[54] FUNGICIDES

[75] Inventors: Paul J. de Fraine, Wokingham; John M. Clough, Marlow; Paul A. Worthington, Maidenhead Court Park; Brian L. Pilkington, Maidenhead; Ian R. Matthews, Wokingham, all of England

[73] Assignee: Zeneca Limited, London, England

[21] Appl. No.: 133,047

[22] PCT Filed: Apr. 14, 1992

[86] PCT No.: PCT/GB92/00681
§ 371 Date: Oct. 12, 1993
§ 102(e) Date: Oct. 12, 1993

[87] PCT Pub. No.: WO92/18487
PCT Pub. Date: Oct. 29, 1992

[30] Foreign Application Priority Data

Apr. 15, 1991 [GB] United Kingdom ............... 9108094
Sep. 27, 1991 [GB] United Kingdom ............... 9120642
Jan. 31, 1992 [GB] United Kingdom ............... 9202071

[51] Int. Cl.[6] ............... A61K 31/505; A61K 31/44; C07D 239/02; C07D 213/56
[52] U.S. Cl. ............... 514/256; 514/357; 544/319; 544/334; 544/335; 546/338
[58] Field of Search ............... 544/319, 334, 335; 546/338; 514/256, 269, 357

[56] References Cited

U.S. PATENT DOCUMENTS 5,055,471 10/1991 de Fraine et al. ............... 514/255
5,104,872 4/1992 Tsubata et al. ............... 514/238

*Primary Examiner*—Cecilia Tsang
*Attorney, Agent, or Firm*—Marian T. Thomson

[57] ABSTRACT

Compounds having formula (I)

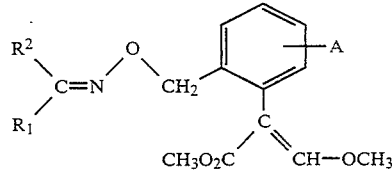

wherein $R^1$, $R^2$ and A are defined as in the specification.

The compounds are useful as fungicides.

8 Claims, No Drawings

FUNGICIDES

This application is a 371 of PCT/GB92/00681, filed Apr. 14, 1992.

This invention relates to derivatives of propenoic acid useful as fungicides, to processes for preparing them, to compositions containing them, and to methods of using them to combat fungi, especially fungal infections of plants.

There are described in EP-A-0 370 629 fungicidal derivatives of propenoic acid which have the general formula (I) wherein A is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$ and $R^2$, which may be the same or different, are hydrogen, optionally substituted alkyl, optionally substituted cycloalkyl, optionally substituted heterocyclylalkyl, optionally substituted cycloalkylalkyl, optionally substituted aralkyl, optionally substituted heteroarylalkyl, optionally substituted aryloxyalkyl, optionally substituted heteroaryloxyalkyl, optionally substituted alkenyl, optionally substituted alkynyl, optionally substituted alkoxy, optionally substituted aryl, optionally substituted heteroaryl, optionally substituted aryloxy, optionally substituted heteroaryloxy, nitro, halo, cyano, $-NR^3R^4$, $-CO_2R^3$, $-CONR^3R^4$, $-COR^3$, $-S(O)_nR^3$ wherein n is 0, 1 or 2, $(CH_2)_mPO(OR^3)_2$ wherein m is 0 or 1, or and $R^1$ and $R^2$ join to form a carbocyclic or heterocyclic ring system; and $R^3$ and $R^4$, which may be the same or different, are hydrogen, optionally substituted alkyl, optionally substituted aralkyl, optionally substituted alkenyl, optionally substituted alkynyl, optionally substituted aryl or optionally substituted heteroaryl. The compounds contain at least one carbon-carbon double bond and one carbon-nitrogen double bond and exist in the form of geometric isomers. The isomers which result from the unsymmetrically substituted double bonds of the propenoate group and the oxime ether are identified by the commonly used terms, "E" and "Z".

The present invention provides a compound of formula (I) wherein $R^1$ is:

(i) pyrid-2-yl substituted by one or more groups selected from $C_{1-6}$ alkoxy, $C_{1-6}$ haloalkyl, $C_{1-6}$ haloalkoxy, $C_{1-4}$ alkoxy($C_{1-6}$)alkyl or $C_{1-4}$ alkoxy($C_{1-6}$)alkoxy;

(ii) the group (A) wherein $Y^1$ is $C_{2-6}$ alkyl, $C_{1-6}$ haloalkyl, $C_{1-6}$ alkoxy, $C_{1-6}$ alkylthio, $C_{1-6}$ alkylsulphinyl, $C_{1-6}$ haloalkoxy, $C_{1-6}$ alkoxy($C_{1-6}$)alkyl, $C_{1-6}$ alkoxy($C_{1-6}$)alkoxy, $C_{1-4}$ alkoxy($C_{1-6}$)alkoxy($C_{1-6}$)alkoxy, di($C_{1-4}$ alkoxy)($C_{1-6}$)alkoxy, $C_{2-6}$ alkenyloxy or $C_{2-6}$ alkynyloxy and $Z^1$ is hydrogen, fluorine, chlorine or $C_{1-6}$ alkyl; or $Y^1$ is methyl and $Z^1$ is fluorine, chlorine or $C_{1-6}$ alkyl; or, (iii) the group (B) wherein $Y^2$ is $C_{2-6}$ alkyl, $C_{1-6}$ haloalkyl, $C_{2-6}$ alkoxy, $C_{1-6}$ alkylthio, $C_{1-6}$ alkylsulphinyl, $C_{1-6}$ haloalkoxy or $C_{2-4}$ alkynyloxy and $Z^2$ is hydrogen, fluorine, chlorine or $C_{1-4}$ alkyl; or $Y^2$ is methyl or methoxy and $Z^2$ is fluorine, chlorine or $C_{1-4}$ alkyl.

The compounds of the invention contain at least one carbon-carbon double bond, and are sometimes obtained in the form of mixtures of geometric isomers. However these mixtures can be separated into individual isomers, and this invention embraces such isomers, and mixtures thereof in all proportions.

The individual isomers which result from the unsymmetrically substituted double bond of the propenoate group are identified by the commonly used terms "E" and "Z". These terms are defined according to the Cahn-Ingold-Prelog system which is fully described in the literature (see, for example, J March, "Advanced Organic Chemistry", 3rd edition, Wiley-Interscience, page 109 et seq).

For the carbon-carbon double bond of the propenoate group, usually one isomer is more active fungicidally than the other, the more active isomer usually being the one wherein the group $-CO_2CH_3$ and $-OCH_3$ are on opposite sides of the olefinic bond of the propenoate group (the (E)-isomer). These (E)-isomers form a preferred embodiment of this invention.

Halogen includes fluorine, chlorine, bromine, and iodine.

Alkyl and the alkyl moieties of alkoxy, haloalkyl and haloalkoxy can be in the form of straight or branched chains and, unless otherwise stated, suitably contain from 1 to 6 carbon atoms. Examples are methyl, ethyl, iso-propyl and tert-butyl.

Examples of haloalkyl and the haloalkyl moiety of haloalkoxy are difluoromethyl, trifluoromethyl, 2,2-difluoroethyl, 2,2,2-trifluoroethyl, 1,1,2,2-tetrafluoroethyl, pentafluoroethyl, 2,2,3,3-tetrafluoroprop-1-yl, 2,2,3,3,3-pentafluoroprop-1-yl, 1,1,1-trifluoroprop-2-yl and 4-fluorobut-1-yl.

Alkenyl and alkynyl moieties of alkenyloxy and alkynyloxy suitably contain from 2 to 6 carbon atoms, typically 2 to 4 carbon atoms, in the form of straight or branched chains. Examples are ethenyl, allyl and propargyl.

In one aspect the present invention provides a compound of formula (I) wherein $Y^1$ is $C_{2-6}$ alkyl, $C_{1-6}$ haloalkyl, $C_{1-6}$ alkoxy, $C_{1-6}$ alkylthio, $C_{1-6}$ alkylsulphinyl, $C_{1-6}$ haloalkoxy or $C_{2-4}$ alkynyloxy and $Z^1$ is hydrogen, fluorine, chlorine or $C_{1-4}$ alkyl; or $Y^1$ is methyl and $Z^1$ is fluorine, chlorine or $C_{1-4}$ alkyl.

In another aspect the present invention provides a compound of formula (I) wherein $Y^1$ is $C_{2-6}$ alkoxy or $C_{1-6}$ haloalkoxy and $Z^1$ is hydrogen, chlorine, fluorine or methyl.

In a further aspect the present invention provides a compound of formula (I) wherein $Y^2$ is $C_{2-6}$ alkoxy or $C_{1-6}$ haloalkoxy and $Z^2$ is hydrogen, chlorine, fluorine or methyl.

According to the present invention there are provided the individual Compounds Nos 1 to 118 having the general formula (I) and the values of $R^1$ given in Table I. All of the compounds in Table I are (E)-propenoates.

TABLE I

| Compound No. | $R^1$ | Olefinic± | Melting Point °C. |
|---|---|---|---|
| 1 | 6-OC$_2$H$_5$-pyrimidin-4-yl | 7.60 | 87–88 |
| 2 | 6-CF$_3$-pyrid-2-yl | 7.60 | Oil |
| 3 | 6-CF$_3$-pyrimidin-4-yl | 7.62 | 87.2–88.4 |
| 4 | 4-CF$_3$-pyrid-2-yl | 7.61 | Oil |
| 5 | 4-CF$_3$-pyrimidin-2-yl | 7.58 | Oil |

TABLE I-continued

| Compound No. | R$^1$ | Olefinic+ | Melting Point °C. |
|---|---|---|---|
| 6 | 4-C$_2$H$_5$O-pyrimidin-2-yl | 7.58 | 87–89 |
| 7 | 6-C$_2$F$_5$-pyrimidin-4-yl | 7.61 | Oil |
| 8 | 4-CH$_3$O-pyrid-2-yl | 7.60 | 60–62 |
| 9 | 4-CH$_3$S-pyrimidin-2-yl | 7.57 | 79–81 |
| 10 | 4-CH$_3$O-pyrimidin-2-yl | 7.58 | Oil |
| 11 | 4-propargyloxy-pyrimidin-2-yl | 7.58 | Solid |
| 12 | 4-n-C$_3$H$_7$O-pyrimidin-2-yl | 7.58 | Oil |
| 13 | 4-n-butyloxy-pyrimidin-2-yl | 7.58 | Oil |
| 14 | 3-CF$_3$-pyrid-2-yl | 7.59 | gum |
| 15 | 4-iso-propyloxypyrimidin-2-yl | 7.58 | 75–77 |
| 16 | 4-C$_2$H$_{O\text{-}pyrid\text{-}2\text{-}yl}$ | 7.59 | gum |
| 17 | 4-C$_2$H$_5$S-pyrimidin-2-yl | 7.58 | 77–79 |
| 18 | 3-CH$_3$O-pyrid-2-yl | 7.58 | 97.1–98.7 |
| 19 | 3-C$_2$H$_5$O-pyrid-2-yl | 7.57 | 83.6–84.3 |
| 20 | 6-CH$_3$O-pyrid-2-yl | 7.60 | 106.2–107.4 |
| 21 | 6-C$_6$H$_5$-pyrimidin-4-yl | 7.61 | 105.4–108 |
| 22 | 4-C$_2$H$_5$O-5-CH$_3$-pyrimidin-2-yl | 7.58 | 80–82 |
| 23 | 4-iso-propyloxy-pyrid-2-yl | 7.60 | Oil |
| 24 | 6-iso-propyloxy-pyrimidin-4-yl | 7.59 | Oil |
| 25 | 4-CF$_3$CH$_2$O-pyrimidin-2-yl | 7.59 | 90–92 |
| 26 | 4-sec-butyloxy-pyrimidin-2-yl | 7.59 | Gum |
| 27 | 4-CH$_3$OC$_2$H$_4$O-pyrid-2-yl | 7.60 | Gum |
| 28 | 4-CH$_3$O-5-CH$_3$-pyrimidin-2-yl | 7.79 | 105–106 |
| 29 | 5-CF$_3$-pyrid-2-yl | 7.60 | Gum |
| 30 | 4-iso-propyloxy-5-CH$_3$-pyrimidin-2-yl | 7.58 | Gum |
| 31 | 4-CF$_3$CH$_2$O-5-CH$_3$-pyrimidin-2-yl | 7.59 | 130–131 |
| 32 | 6-C$_2$H$_5$O-pyrid-2-yl | 7.60 | 64.4–65.6 |
| 33 | 4-CH$_2$H$_5$O-5-F-pyrimidin-2-yl | 7.58 | 100–102 |
| 34 | 4-CH$_3$O-5-F-pyrimidin-2-yl | 7.58 | 79–81 |
| 35 | 6-CF$_3$CH$_2$O-pyrimidin-4-yl | 7.61 | Gum |
| 36 | 4-CF$_3$-6-CF$_3$CH$_2$O-pyrid-2-yl | 7.61 | 84.1–85.1 |
| 37 | 4-CF$_3$CH$_2$O-5-F-pyrimidin-2-yl | 7.58 | 88–89 |
| 38 | 4-iso-propyloxy-5-F-pyrimidin-2-yl | 7.58 | 89–91 |
| 39 | 4-CF$_3$-6-C$_2$H$_5$O-pyrid-2-yl | 7.60 | Gum |
| 40 | 4-CHF$_2$CF$_2$CH$_2$O-pyrimidin-2-yl | 7.58 | 76–78 |
| 41 | 4-CF$_3$-6-CH$_3$O-pyrid-2-yl | 7.61 | 80.3–80.8 |
| 42 | 4-CF$_3$CH$_2$O-pyrid-2-yl | 7.60 | 130.0–131.8 |
| 43 | 5-iso-propyl-6-CH$_3$O-pyrimidin-4-yl | 7.58 | Gum |
| 44 | 4-iso-butyloxy-pyrimidin-2-yl | 7.58 | 65–68 |
| 45 | 5-C$_2$H$_5$-6-CF$_3$-pyrimidin-4-yl | 7.59 | Gum |
| 46 | 4-tert-butyloxy-pyrimidin-2-yl | 7.58 | Gum |
| 47 | 4-C$_2$H$_5$O-5-Cl-pyrimidin-2-yl | 7.58 | 120–122 |
| 48 | 4-allyloxy-pyrimidin-2-yl | 7.57 | Gum |
| 49 | 4-iso-propyloxy-5-Cl-pyrimidin-2-yl | 7.58 | 90–92 |
| 50 | 4-CF$_3$CH$_2$O-5-Cl-pyrimidin-2-yl | 7.58 | 114–115 |
| 51 | 4-CF$_3$CF$_2$CH$_2$O-pyrimidin-2-yl | 7.59 | 108–110 |
| 52 | 4-(2-methylprop-2-enyl)oxy-pyrimidin-2-yl | 7.58 | Gum |
| 53 | 6-CF$_3$CH(CH$_3$)O-pyrimidin-4-yl | 7.62 | Gum |
| 54 | 4-CH$_3$O-5-Cl-pyrimidin-2-yl | 7.58 | 134–6 |
| 55 | 4-CHF$_2$CH$_2$O-pyrimidin-2-yl | | |
| 56 | 4-CH$_2$FCH$_2$CH$_2$O-pyrimidin-2-yl | | |
| 57 | 4-CF$_3$CH(CH$_3$)O-pyrimidin-2-yl | | |
| 58 | 4-CH$_2$FCH$_2$CH$_2$CH$_2$O-pyrimidin-2-yl | | |
| 59 | 4-CF$_3$CH$_2$CH$_2$CH$_2$O-pyrimidin-2-yl | | |
| 60 | 4-CF$_3$CF$_2$CH(CH$_3$)O-pyrimidin-2-yl | | |
| 61 | 4-CHF$_2$CF$_2$CH(CH$_3$)O-pyrimidin-2-yl | | |
| 62 | 4-CH$_3$CHFCF$_2$CH$_2$O-pyrimidin-2-yl | | |
| 63 | 4-CF$_3$CF$_2$CF$_2$CH$_2$O-pyrimidin-2-yl | | |
| 64 | 4-CF$_3$CF$_2$CF$_2$CF$_2$O-pyrimidin-2-yl | | |
| 65 | 4-CH$_3$OCH$_2$CH$_2$O-pyrimidin-2-yl | | |
| 66 | 4-CH$_3$CH$_2$OCH$_2$CH$_2$O-pyrimidin-2-yl | 7.57 | Gum |
| 67 | 4-CH$_3$(CH$_2$)$_4$O-pyrimidin-2-yl | | |
| 68 | 4-CH$_3$(CH$_2$)$_2$CH(CH$_3$)O-pyrimidin-2-yl | | |
| 69 | 4-iso-propyl-6-C$_2$H$_5$O-pyrimidin-4-yl | | |
| 70 | 5-iso-propyl-6-CF$_3$CH$_2$O-pyrimidin-4-yl | | |
| 71 | 6-(CF$_3$)$_2$CHO-pyrimidin-4-yl | | |
| 72 | 6-CHF$_2$CH$_2$O-pyrimidin-4-yl | | |
| 73 | 6-CH$_2$FCH$_2$CH$_2$O-pyrimidin-4-yl | | |
| 74 | 6-CH$_2$FCH$_2$CH$_2$CH$_2$O-pyrimidin-4-yl | | |
| 75~ | 6-CF$_3$CH$_2$CH$_2$CH$_2$O-pyrimidin-4-yl | | |
| 76 | 6-CF$_3$CF$_2$CH(CH$_3$)O-pyrimidin-4-yl | | |
| 77 | 6-CHF$_2$CF$_2$CH(CH$_3$)O-pyrimidin-4-yl | | |
| 78 | 6-CF$_3$CHFCF$_2$CH$_2$O-pyrimidin-4-yl | | |
| 77 | 6-CF$_3$CF$_2$CF$_2$CH$_2$O-pyrimidin-4-yl | | |
| 78 | 6-CF$_3$CHFCF$_2$CH$_2$O-pyrimidin-4-yl | | |
| 79 | 6-CF$_3$CF$_2$CF$_2$CH$_2$O-pyrimidin-4-yl | | |
| 80 | 5-F-6-CF$_3$CH$_2$O-pyrimidin-4-yl | | |
| 81 | 5-Cl-6-CF$_3$CH$_2$O-pyrimidin-4-yl | | |
| 82 | 5-CH$_3$-6-CF$_3$CH$_2$O-pyrimidin-4-yl | | |
| 83 | 5-CH$_3$CH$_2$-6-CF$_3$CH$_2$O-pyrimidin-4-yl | | |

TABLE I-continued

| Compound No. | R¹ | Olefinic+ | Melting Point °C. |
|---|---|---|---|
| 84 | 5-CH₃CH₂CH₂-6-CF₃CH₂-pyrimidin-4-yl | | |
| 85 | 3-CH₃O-4-CF₃-pyrid-2-yl | | |
| 86 | 3-CH₃CH₂O-4-CF₃-pyrid-2-yl | | |
| 87 | 5-CH₃CH₂O-pyrid-2-yl | | |
| 88 | 4-CH₃CH₂OCH₂CH₂CH₂O-pyrimidin-2-yl | | |
| 89 | 4-CH₃OCH₂CH₂CH₂O-pyrimidin-2-yl | | |
| 90 | 4-CH₃CH₂OCH₂CH₂CH(CH₃CH₂)-O-pyrimidin-2-yl | | |
| 91 | 4-CH₃OCH₂CH₂CH₂OCH₂CH₂CH₂O-pyrimidin-2-yl | | |
| 92 | 4-CH₃OCH(CH₃)CH₂O-pyrimidin-2-yl | | |
| 93 | 4-CH₃CH₂OCH₂CH(CH₂OCH₂CH₃)-O-pyrimidin-2-yl | | |
| 94 | 4-CH₃OCH₂CH(CH₃)O-pyrimidin-2-yl | | |
| 95 | 4-CH₃(CH₂)₃OCH₂CH(CH₃))-pyrimidin-2-yl | | |
| 96 | 4-CH₃OCH₂CH(CH₂CH₃)O-pyrimidin-2-yl | | |
| 97 | 4-CH₃CH₂OCH₂CH(CH₃)O-pyrimidin-2-yl | | |
| 98 | 4-CH₃OCH₂O-pyrimidin-2-yl | | |
| 99 | 4-CH₃CH₂OCH₂O-pyrimidin-2-yl | | |
| 100 | 4-CH₃CH₂OCH(CH₃)O-pyrimidin-2-yl | | |
| 101 | 4-C₂H₅-pyrimidin-2-yl | | |
| 102 | 4-allyloxy-5-CH₃-pyrimidin-2-yl | | |
| 103 | 4,5-di-CH₃-pyrimidin-2-yl | | |
| 104 | 4-(3-butenyloxy)-pyrimidin-2-yl | | |
| 105 | 4-(2-methyl-2-propenyloxy)-pyrimidin-2-yl | | |
| 106 | 4-(2-butynyloxy)-pyrimidin-2-yl | | |
| 107 | 4-(3-butynyloxy)-pyrimidin-2-yl | | |
| 108~ | 4-(3-buten-2-yloxy)-pyrimidin-2-yl | | |
| 109~ | 4-(2-butenyloxy)-pyrimidin-2-yl | | |
| 110~ | 4-(butyn-3-yloxy)-pyrimidin-2-yl | | |
| 111 | 4-F₂CHO-pyrimidin-2-yl | | |
| 112 | 6-F₂CHO-pyrimidin-4-yl | | |
| 113 | 4-CF₃O-pyrimidin-2-yl | | |
| 114 | 6-CF₃O-pyrimidin-4-yl | | |
| 115 | 4-CHF₂CF₂O-pyrimidin-2-yl | | |
| 116 | 6-CHF₂CF₂O-pyrimidin-4-yl | | |
| 117 | 4-CCl₃O-pyrimidin-2-yl | | |
| 118 | 6-CCl₃O-pyrimidin-4-yl | | |

+Chemical shift of singlet from olefinic proton on β-methoxypropenoate group of major oxime ether isomer (ppm from tetramethylsilane).
~In the form of a gum, NMR data given in Table II.

The compounds of the invention are characterized by the melting points given in Table I and/or by the NMR data given in Table II.

TABLE II

SELECTED PROTON NMR DATA

| Compound No. | Proton NMR Data (δ) |
|---|---|
| 2 | 2.34(3H, s); 3.69(3H, s); 3.82(3H, s); 5.19(2H, s); 7.10–7.60(5H, m); 7.60(1H, s); 7.79(1H, t); 8.08(1H, d) ppm. |
| 5 | 2.40(3H, s); 3.68(3H, s); 3.82(3H, s); 5.35(2H, s); 7.18(1H, m); 7.35(2H, m); 7.54(1H, m); 7.58(1H, s); 7.60(1H, d); 9.07(1H, d) ppm. |
| 7 | 2.30(3H, s); 3.68(3H, s); 3.83(3H, s); 5.25(2H, s); 7.18(1H, m); 7.35(2H, m); 7.48(1H, m); 7.61(1H, s); 8.22(1H, s); 9.33(1H, s) ppm. |
| 10 | 2.35(3H, s); 3.68(3H, s); 3.82(3H, s); 4.03(3H, s); 5.30(2H, s); 6.68(1H, d); 7.18(1H, m); 7.34(2H, m); 7.54(1H, s); 7.58(1H, s); 8.50(1H, d) ppm. |
| 11 | 2.35(3H, s); 2.51(1H, m); 3.68(3H, s); 3.82(3H, s); 5.05(2H, d); 5.32(2H, s); 6.76(1H, d); 7.18(1H, m); 7.34(2H, m); 7.55(1H, m); 7.58(1H, s); 8.58(1H, d) ppm. |
| 12 | 1.03(3H, t); 1.81(2H, m); 2.35(3H, s); 3.68(3H, s); 3.82(3H, s); 4.36(2H, t); 5.31(2H, s); 6.65(1H, d); 7.18(1H, m); 7.35(2H, m); 7.55(1H, d); 7.58(1H, s); 8.50(1H, d) ppm. |
| 13 | 0.99(3H, t); 1.48(2H, m); 1.78(2H, m); 2.35(3H, s); 3.68(3H, s); 3.82(3H, s); 4.41(2H, t); 5.31(2H, s); 6.65(1H, d); 7.18(1H, m); 7.32(2H, m); 7.55(1H, d); 7.58(1H, s); 8.49(1H, d) ppm. |
| 14 | 2.29(3H, s); 3.68(3H, s); 3.80(3H, s); 5.14(2H, s) 7.16(1H, m); 7.28–7.43(3H, m); 7.51(1H, m); 7.59(1H, s); 8.02(1H, d); 8.77(1H, d) ppm. |
| 16 | 1.43(3H, t); 2.32(3H, s); 3.69(3H, s); 3.80(3H, s); 4.10(2H, q); 5.19(2H, s); 6.75(1H, m); 7.16(1H, m); 7.29–7.39(3H, m); 7.52(1H, m); 7.59(1H, s); 8.38(1H, d) ppm. |
| 23 | 1.36(6H, d); 2.32(3H, s); 3.69(3H, s); 3.82(3H, s); 4.69(1H, m); 5.18(2H, s); 6.73(1H, dd); 7.17(1H, m); 7.28–7.37(3H, m); 7.52(1H, m); 7.60(1H, s); 8.38(1H, d) ppm. |
| 24 | 1.35(6H, d); 2.26(3H, s); 3.69(3H, s); 3.82(3H, s); 5.18(2H, s); 5.37(1H, m); 7.11(1H, s); 7.1–7.5(4H, m); 7.59(1H, s); 8.73(1H, s) ppm. |
| 26 | 0.98(3H, t); 1.36(3H, d); 1.72(2H, m); 2.32(3H, s); 3.68(3H, s); 3.82(3H, s); 5.28(2H, s); 5.32(2H, s); 6.61(1H, d); 7.18(1H, m); 7.35(2H, m); 7.55(1H, m); 7.59(1H, s); 8.49(1H, d) ppm. |
| 27 | 2.32(3H, s); 3.45(3H, s); 3.69(3H, s); 3.76(2H, t); 3.82(3H, s); 4.20(2H, t); 5.18(2H, s); 6.81(1H, dd); 7.17(1H, m); 7.29–7.37(2H, m); 7.42(1H, d); 7.51(1H, m); 7.60(1H, s); 8.39(1H, d) ppm. |
| 29 | 2.33(3H, s); 3.70(3H, s); 3.83(3H, s); 5.21(2H, s); 7.18(1H, t); 7.34(2H, t); 7.50(1H, t); 7.60(1H, s); 7.85(1H, dd); 8.02(1H, d); 8.82(1H, s) ppm. |
| 30 | 1.38(6H, d); 2.12(3H, s); 2.34(3H, s); 3.68(3H, S); 3.82(3H, s); 5.29(2H, s); 5.47(1H, m); 7.18(1H, m); 7.34(2H, m); 7.55(1H, s); 7.58(1H, s); 8.30(1H, s) ppm. |
| 35 | 2.27(3H, s); 3.70(3H, s); 3.85(3H, s); 4.81(2H, q); 5.19(2H, s); 7.18(1H, m); 7.34(3H, m); 7.48(1H, m); 7.61(1H, s); 8.86(1H, s) ppm. |
| 39 | 1.40(3H, t); 2.28(3H, s); 3.69(3H, s); 3.84(3H, s); 4.42(2H, q); 5.19(2H, s); 6.87(1H, s); 7.16(1H, m); 7.34(2H, m); 7.51(1H, m); 7.60(1H, s); 7.67(1H, s) ppm. |
| 43 | 1.18(6H, d); 2.21(3H, s); 3.19(1H, sept); 3.67(3H, s); 3.81(3H, s); 3.99(3H, s); 5.10(2H, s); 7.16(1H, m); 7.33(1H, m); 7.48(1H, m); 7.57(1H, s); 8.59(1H, s) ppm. |
| 45 | 1.00(3H, t); 2.29(3H, s); 2.91(2H, q); 3.67(3H, s); 3.82(3H, s); 5.16(2H, s); 7.17(1H, m); 7.34(2H, m); 7.45(1H, m); 7.54(1H, s); 9.15(1H, s) ppm. |

TABLE II -continued
SELECTED PROTON NMR DATA

| Compound No. | Proton NMR Data (δ) |
|---|---|
| 46 | 1.61(9H, s); 2.30(3H, s); 3.68(3H, s); 3.82(3H, s); 5.30(2H, s); 6.55(1H, d); 7.18(1H, m); 7.34(1H, m); 7.55(1H, m); 7.58(1H, s); 8.45(1H, d) ppm. |
| 48 | 2.35(3H, s); 3.69(3H, s); 3.81(3H, s); 4.92(2H, d); 5.2–5.5(1H, m); 5.31(2H, s); 6.0–6.2(1H, m); 6.70(1H, d); 7.1–7.6(4H, m); 7.57(1H, s); 8.53(1H, d) ppm. |
| 52 | 1.83(3H, s); 2.35(3H, s); 3.69(3H, s); 3.82(3H, s); 4.86(2H, s); 5.00(1H, s); 5.10(1H, s); 5.31(2H, s); 6.72(1H, d); 7.1–7.6(4H, m); 7.58(1H, s); 8.54(1H, d) ppm. |
| 53 | 1.50(3H, d); 2.27(3H, s); 3.71(3H, s); 3.85(3H, s); 5.19(2H, s); 5.83(1H, sept); 7.09(1H, m); 7.28(1H, s); 7.35(2H, m); 7.49(1H, m); 7.62(1H, s); 8.76(1H, s) ppm. |
| 66 | 1.24(3H, t); 2.34(3H, s); 3.60(2H, q); 3.68(3H, s); 3.81(2H, m); 3.83(3H, s); 4.58(2H, m); 5.32(2H, s); 6.74(1H, d); 7.1–7.6(4H, m); 7.57(1H, s); 8.53(1H, d) ppm. |
| 75 | 2.06(2H, m); 2.27(3H, s); 2.27(2H, m); 3.70(3H, s); 3.84(3H, s); 4.43(2H, t); 5.20(2H, s); 7.18(1H, m); 7.20(1H, s); 7.35(2H, m); 7.49(1H, m); 7.61(1H, s); 8.75(1H, s) ppm. |
| 108 | 1.45(3H, d); 2.32(3H, s); 3.68(3H, s); 3.82(3H, s); 5.18(1H, d); 5.32(1H, d); 5.31(2H, s); 5.78(1H, m); 5.92(1H, m); 6.62(1H, d); 7.17(1H, m); 7.33(2H, m); 7.55(1H, m); 7.58(1H, s); 8.50(1H, d) ppm. |
| 109 | 1.77(3H, d); 2.34(3H, s); 3.68(3H, s); 3.82(3H, s); 4.86(2H, d); 5.31(2H, s); 5.67–5.99(2H, m); 6.67(1H, d); 7.15(1H, m); 7.34(2H, m); 7.54(1H, m); 7.58(1H, s); 8.50(1H, d) ppm. |
| 110 | 1.66(3H, d); 2.36(3H, s); 2.47(1H, s); 3.68(3H, s); 3.81(3H, s); 5.31(2H, s); 5.87(1H, m); 6.71(1H, d); 7.1–7.6(4H, m); 7.57(1H, d); 8.56(1H, d) ppm. |

Table II shows selected proton NMR data for certain compounds described in Table I. Chemical shifts are measured in ppm from tetramethylsilane, and deuterochloroform was used as solvent throughout. The operating frequency of the NMR spectrometer was 270 MHz. The following abbreviations are used:
s = singlet
sept = septet
d = doublet
m = multiplet
dd = double doublet
br = broad
t = triplet
ppm = parts per million
q = quartet The compounds of the invention of formula (I) may be prepared by the steps shown in Scheme 1. The term $R^1$ is as defined above, and X is a leaving group (such as halogen (chlorine, bromine or iodine) or $OSO_2CF_3$).

The compounds of formula (I) may be prepared by reacting a compound of formula (II) with the salt of an oxime of formula (III) under basic conditions. Thus an oxime of general formula (III) may be treated with a suitable base (such as sodium hydride or sodium methoxide), in a suitable solvent (such as N,N-dimethylformamide or tetrahydrofuran), to form the anion and then a compound of formula (II) added.

Oximes of the general formula (III) are known in the chemical literature. The compound of general formula (II) where X is bromine and the propenoate group has the (E)-configuration is described in EP-A-0203606.

Oximes of formula (III) can be prepared by reacting a compound of formula (XI) with hydroxylamine in a suitable solvent (for example a mixture of a primary alcohol (such as methanol or ethanol) with water) optionally in the presence of a buffer (such as a salt of an organic acid (for example sodium acetate)).

Compounds of formula (XI) can be prepared by treating a compound of formula (XII) with an acid, preferably a strong mineral acid such as hydrochloric acid of suitable concentration, in a suitable solvent, for example acetone. Compounds of formula (XII) can be prepared by treating a compound of formula (XIII) (wherein X is typically chlorine, bromine or $OSO_2CF_3$) with an alkoxyvinyl tin (for example (1-ethoxyvinyl)tri-n-butyltin) in the presence of a suitable catalyst (such as bis(triphenylphosphine)palladium(II) chloride) in a suitable solvent (for example N,N-dimethylformamide).

Alternatively, compounds of formula (XI) can be prepared by reacting a compound of formula (XIV) with a methyl magnesium halide in a suitable solvent (for example diethyl ether or tetrahydrofuran). Compounds of formula (XIV) can be prepared by reacting a compound of formula (XIII) with a trialkylamine (such as trimethylamine) which is preferably in aqueous solution, and in the presence of a suitable organic solvent (for example diethyl ether), and then introducing a source of cyanide anions (for example potassium or sodium cyanide).

Alternatively, compounds of formulae (XI), (XII), (XIII) and (XIV) can be prepared by methods known in the literature.

Alternatively, compounds of formula (I) can be prepared by treating the substituted hydroxylamine (XV) (or a salt thereof, for example its hydrochloride salt) with a compound of formula (XI). The substituted hydroxylamine (XV) wherein A is hydrogen may be prepared as described in EP 0 463 488.

Alternatively compounds of the invention of formula (I) may be prepared by the steps shown in Scheme 2. The terms $R^1$ and X are as defined above, $R^5$ is hydrogen or a metal (such as sodium or potassium), and R is an alkyl group. Each transformation is performed at a suitable temperature and usually, though not always, in a suitable solvent.

The compounds of the invention of formula (I) can be prepared from phenylacetates of formula (VI) or the ketoesters of formula (X) by the steps shown in Scheme 2.

Thus compounds of formula (I) can be prepared by treatment of phenylacetates of formula (VI) with a base (such as sodium hydride or sodium methoxide) and methyl formate. If a species of formula $CH_3L$, wherein L is a leaving group such as a halide (chlorine, bromine or iodine), or a $CH_3SO_4$ anion, is then added to the reaction mixture, compounds of formula (I) may be obtained. If a protic acid is added to the reaction mixture, compounds of formula (IX) wherein $R^5$ is hydrogen, are obtained. Alternatively the species of formula (IX) wherein $R^5$ is a metal (such as sodium), may themselves be isolated from the reaction mixture.

Compounds of formula (IX) wherein $R^5$ is a metal can be converted into compounds of formula (I) by treatment with a species $CH_3L$, wherein L is as defined above. Compounds of formula (IX) wherein $R^5$ is hydrogen can be converted into compounds of formula (I) by successive treatment with a base (such as potassium carbonate) and a species of general formula $CH_3L$.

Alternatively, compounds of formula (I) can be prepared from acetals of formula (IV) by elimination of methanol under either acidic or basic conditions. Examples of reagents or reagent mixtures which can be used for this transformation are lithium di-isopropylamide; potassium hydrogen sulphate (see, for example, T. Yamada, H. Hagiwara and H. Uda, *J. Chem. Soc. Chemical Communications*, 1980, 838, and references therein); and triethylamine, often in the presence of a Lewis acid such as titanium tetrachloride (see, for example, K. Nsunda and L. Heresi, *J. Chem. Soc. Chemical Communications*, 1985, 1000).

Acetals of formula (IV) can be prepared by treatment of methyl silyl ketene acetals of formula (V) with trimethyl orthoformate in the presence of a Lewis acid such as titanium tetrachloride (see, for example, K. Saigo, M. Osaki and T. Mukaiyama, *Chemistry Letters*, 1976, 769).

Methyl silyl ketene acetals of formula (V) can be prepared from phenylacetates of formula (VI) by treatment with a base and trialkylsilyl halide of formula $R_3SiCl$ or $R_3SiBr$, such as trimethylsilyl chloride, or a base (such as triethylamine) and a trialkylsilyl triflate of formula $R_3Si—OSO_2CF_3$ (see, for example, C. Ainsworth, F. Chen and Y. Kuo, *J. Organometallic Chemistry*, 1972, 46, 59).

It is not always necessary to isolate the intermediates (IV) and (V); under appropriate conditions compounds of formula (I) may be prepared from phenylacetates of formula (VI) in "one pot" by the successive addition of suitable reagents listed above.

Phenylacetates of formula (VI) may be prepared from phenylacetates of formula (VII). Thus, if an oxime of general formula (III) is treated with a suitable base (such as sodium hydride or sodium methoxide) and the phenyl acetates of formula (VII) are added, phenylacetates of formula (VI) are obtained.

Phenylacetates of formula (VII) can be obtained from isochromanones of formula (VIII) by treatment with HX, wherein X is a halogen (such as bromine), in methanol. This transformation may also be accomplished in 2 steps if the isochromanone (VIII) is treated with HX in a non-alcoholic solvent, and the resulting phenylacetic acid is then esterified using standard procedures (see, for example, I. Matsumoto and J. Yoshizawa, Jpn. Kokai (Tokkyo Koho) 79 138 536, 27.10.1979, *Chem. Abs.*, 1980, 92, 180829h; and G. M. F. Lim, Y. G. Perron and R. D. Droghini, *Res. Discl.*, 1979, 188, 672, *Chem. Abs.*, 1980, 92, 128526t). Isochromanones of formula (VIII) are well known in the chemical literature.

Alternatively, compounds of formula (I) can be prepared by treatment of ketoesters of formula (X) with methoxymethylenation reagents such as methoxymethylenetriphenylphosphorane (see, for example, W. Steglich, G. Schramm, T. Anke and F. Oberwinkler, EP 0044 448, 4.7.1980).

Ketoesters of formula (X) may be prepared from ketoesters of formula (VI), by treatment with the anion of oximes of general formula (III) as described above. Ketoesters of formula (XVI) are described in EP 0331 061.

Therefore, to summarise, Schemes 1 and 2 illustrate certain methods by which the oxime ether and the 3-methoxypropenoate moieties, respectively, may be constructed in the final stages of the synthesis of the compounds of the invention of formula (I). An alternative final stage or stages in the synthesis of the compounds of the invention of formula (I) is a modification to the group $R^1$. Thus, for example, if a substituent on the group $R^1$ is a suitably positioned amino group, it may be converted in the final stages of the reaction sequence through diazotisation into a halogen atom.

In a further aspect the present invention provides a process for the preparation of a compound of formula (I).

In other aspects the present invention provides the intermediate compounds 2-acetyl-4-(2,2,2-trifluoroethoxy)pyrimidine.

The compounds of the invention are active fungicides and may be used to control one or more of the following pathogens: *Pyricularia oryzae* on rice. *Puccinia recondita*, *Puccinia striiformis* and other rusts on wheat, *Puccinia hordei*, *Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. *Helminthosporium* spp., *Rhynchosporium* spp., *Septoria* spp., *Pyrenophora* spp., *Pseudocercosporella herpotrichoides* and *Gaeumannomyces graminis* on cereals. *Cercospora arachidicola* and *Cercosporidium personata* on peanuts and other Cercospora species on other hosts, for example, sugar beet, bananas, soya beans and rice. *Botrytis cinerea* (grey mould) on tomatoes, strawberries, vegetables, vines and other hosts. *Alternaria* spp. on vegetables (e.g. cucumber), oil-seed rape, apples, tomatoes and other hosts. *Venturia inaequalis* (scab) on apples. *Plasmopara viticola* on vines. Other downy mildews such as *Bremia lactucae* on lettuce, *Peronospora* spp. on soybeans, tobacco, onions and other hosts, *Pseudoperonospora humuli* on hops and *Pseudoperonospora cubensis* on cucurbits. *Phytophthora infestans* on potatoes and tomatoes and other Phytophthora spp. on vegetables, strawberries, avocado, pepper, ornamentals, tobacco, cocoa and other hosts. *Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against *Fusarium* spp., *Septoria* spp., *Tilletia* spp., (bunt, a seed-borne disease of wheat), *Ustilago* spp. and *Helminthosporium* spp. on cereals, *Rhizoctonia solani* on cotton and *Pyricularia oryzae* on rice.

The compounds may have systemic movement in plants. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides a fungicidal composition comprising, as an active ingredient, a compound as hereinbefore defined and a fungicidally acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler.

Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (±)-2-

(2,4-dichlorophenyl)-3-(1H-1,2,4-triazol-1-yl)propyl 1,1,2,2-tetrafluoroethyl ether, (RS)-1-aminopropylphosphonic acid, (RS)-4-(4-chlorophenyl)-2-phenyl-2-(1H-1,2,4-triazol-1-ylmethyl)butyronitrile, (RS)-chloro-N-(cyano(ethoxy)methyl)benzamide, (Z)-N-but-2-enyloxymethyl-2-chloro-2',6'-diethylacetanilide, 1-(2-cyano-2-methoxyiminoacetyl)-3-ethyl urea, 1-[2RS,4RS;2RS,4RS)-4-bromo-2-(2,4-dichlorophenyl)-tetrahydrofurfuryl]-1H-1,2,4-triazole, 3-(2,4-dichlorophenyl)-2-(1H-1,2,4-triazol-1-yl)quinazolin-4(3H)-one, 3-chloro-4-[4-methyl-2-(1H-1,2,4-triazol-1-methyl)-1,3-dioxolan-2-yl]phenyl-4-chlorophenyl ether, 4-bromo-2-cyano-N,N-dimethyl-6-trifluoromethylbenzimidazole-1-sulphonamide, 4-chlorobenzyl N-(2,4-dichlorophenyl)-2-(1H-1,2,4-triazol-1-yl)thioacetamidate, 5-ethyl-5,8-dihydro-8-oxo(1,3)-dioxolo(4,5-g)quinoline-7-carboxylic acid, α-[N-(3-chloro-2,6-xylyl)-2-methoxyacetamido]-γ-butyrolactone, anilazine, BAS 454, benalaxyl, benomyl, biloxazol, binapacryl, bitertanol, blasticidin S, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, dimethamorph, dimethirimol, diniconazole, dinocap, ditalimfos, dithianon, dodemorph, dodine, edifenphos, etaconazole, ethirimol, ethyl (Z)-N-benzyl-N-([methy(methylthioethylideneaminooxycarbonyl)amino]thio)-β-alaninate, etridazole, fenapanil, fenarimol, fenfuram, fenpiclonil, fenpropidin, fenpropimorph, fentin acetate, fentin hydroxide, flutolanil, flutriafol, fluzilazole, folpet, fosetyl-aluminium, fuberidazole, furalaxyl, furconazole-cis, guazatine, hexaconazole, hydroxyisoxazole, imazalil, iprobenfos, iprodione, isoprothiolane, kasugamycin, mancozeb, maneb, mepronil, metalaxyl, methfuroxam, metsulfovax, myclobutanil, neoasozin, nickel dimethyldithiocarbamate, nitrothal-isopropyl, nuarimol, ofurace, organomercury compounds, oxadixyl, oxycarboxin, penconazole, pencycuron, pent-4-enyl N-furfuryl-N-imidazol-1-ylcarbonyl-DL-homoalaninate, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, techlofthalam, tecnazene, tebuconazole, thiabendazole, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses). Examples of suitable plant growth regulating compounds for use with the invention compounds are 3,6-dichloropicolinic acid, 1-(4-chlorophenyl-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. Throughout the Examples, the term 'ether' refers to diethyl ether, magnesium sulphate was used to dry solutions, and solutions were concentrated under reduced pressure. Reactions involving air or water sensitive intermediates were performed under an atmosphere of nitrogen and solvents were dried before use, where appropriate. Unless otherwise stated, chromatography was performed on a column of silica gel as the stationary phase. Where shown, infrared and NMR data are selective; no attempt is made to list every absorption in all cases. $^1$H NMR spectra were recorded using $CDCl_3$-solutions unless otherwise stated. The following abbreviations are used throughout:

| | | |
|---|---|---|
| DMF = N,N-dimethylformamide | m.p. = melting point | t = triplet |
| | ppm = parts per million | q = quartet |
| NMR = nuclear magnetic resonance | s = singlet | m = multiplet |
| | d = doublet | br = broad |
| IR = infrared | | |
| b.p. = boiling point | | |

EXAMPLE 1

This Example illustrates the preparation of (E),(E)-methyl 2-[2-(4-trifluoromethylpyrid-2-yl-acetoximinomethyl)phenyl]-3-methoxypropenoate (Compound No. 4 of Table I).

A solution of 2-chloro-4-trifluoromethylpyridine (3.33 g), (1-ethoxyvinyl)tri-n-butyltin (5.95 g) and bis(triphenylphosphine)palladium(II) chloride (0.4 g) in DMF (40 ml) was heated at 70° C. for 16 hours. The reaction mixture was cooled to room temperature, potassium fluoride (60 ml of a 10% aqueous solution) was added and the resulting mixture was stirred for 1 hour then filtered through Hyflo supercel filter aid which was rinsed through with ether. The filtrate was extracted with ether (×2) and the combined extracts were washed with brine, then dried, concentrated and chromatographed using ether:hexane 1:4 as the eluant to give 1-ethoxy-1-(4-trifluoromethylpyrid-2-yl)-ethylene (1.4 g, 35% yield) as a pale yellow liquid; $^1$H NMR (270 MHz): δ1.45(3H,t), 4.00(2H,q), 4.42(1H,d), 5.50(1H,d), 7.40(1H,d), 7.88(1H,s), 8.72(1H,d) ppm.

A solution of 1-ethoxy-1-(4-trifluoromethylpyrid-2-yl)-ethylene (1.4 g) in acetone (15 ml) was treated with hydrochloric acid (5 ml of a 2M solution). The reaction mixture was allowed to stand for 16 hours then concentrated, diluted with water and neutralised with sodium bicarbonate. The aqueous phase was extracted with ether (×2) and the combined extracts were washed with brine, dried and concentrated to give 2-acetyl-4-trifluoromethylpyridine (1.2 g, 99% yield) as a pale yellow liquid. IR maximum (film): 1705 cm$^{-1}$.

A solution of 2-acetyl-4-trifluoromethylpyridine (1.2 g), hydroxylamine (0.495 g) and sodium acetate (2.2 g) in a mixture of ethanol:water (20:10 ml) was heated under reflux for 2 hours. The reaction mixture was poured into water and extracted with ethyl acetate (×2). The combined extracts were washed with water, dried and concentrated to give a solid which was washed with hexane to give (E)-2-acetyl-4-trifluoromethylpyridine oxime (1.0 g, 77% yield) as a pale pink solid; $^1$H NMR (270 MHz): δ2.39(3H,s), 7.47(1H,d), 7.89(1H,brs), 8.12(1H,s), 8.12(1H,s), 8.78(1H,d); ppm.

A solution of 2-acetyl-4-trifluoromethylpyridine oxime (0.66 g) in DMF (10 ml) was added dropwise to a stirred suspension of sodium hydride (0.078 g) in DMF (20 ml). An hour later, the reaction mixture was cooled to 0° C. and a solution of (E)-methyl-2-[2-(bromomethyl)phenyl]-3-methoxypropenoate (0.92 g) in DMF (10 ml) was added dropwise. After a further 2 hours, the reaction mixture was poured into water and extracted with ether (×3). The organic extracts were washed with brine, dried, concentrated and chromatographed using ethyl acetate:hexane 3:7 as the eluant to give the title compound (0.844 g, 64% yield) as a colourless oil; IR maxima (film): 1708, 1633 cm$^{-1}$; $^1$H NMR (270 MHz): δ2.33(3H,s), 3.69(3H,s), 3.82(3H,s), 5.20(2H,s), 7.18(1H,m), 7.35(2H,m), 7.45(1H,d), 7.50(1H,m), 7.61(1H,s), 8.14(1H,s), 8.75(1H,d) ppm.

EXAMPLE 2

This Example illustrates the preparation of (E),(E)-methyl 2-[2-(4-ethoxypyrimidin-2-yl-acetoximino-methyl)phenyl]-3-methoxypropenoate (Compound No. 6 of Table I).

A solution of 2-chloro-4-ethoxypyrimidine (6.34 g), (1-ethoxyvinyl)-tri-n-butyltin (14.4 g) and bis(triphenylphosphine)palladium(II) chloride (1 g) in DMF (60 ml) was heated at 90° C. for 60 hours. The reaction mixture was cooled to room temperature and potassium fluoride (100 ml of a 10% aqueous solution) was added. The resulting mixture was stirred for 1 hour then filtered through Hyflo supercel filter aid which was rinsed through with ether. The filtrate was extracted with ether (×2) and the combined extracts were washed with brine, then dried, concentrated and chromatographed using ethyl acetate:hexane 1:4 as the eluant to give 1-ethoxy-1-(4-ethoxypyrimidin-2-yl)-ethylene (2.7 g, 35% yield) as an orange oil; IR maximum (film): 1550cm$^{-1}$; $^1$H NMR (270 MHz): δ1.40(3H,t), 1.50(3H,t), 4.02(2H,q), 4.45(2H,q), 4.58(1H,d), 5.65(1H,d), 6.60(1H,d), 8.48(1H,d) ppm.

A solution of 1-ethoxy-1-(4-ethoxypyrimidin-2-yl)-ethylene (2.7 g) in acetone (20 ml) was treated with hydrochloric acid (6 ml of a 2M solution). The reaction mixture was allowed to stand for 16 hours, then warmed at 40° C. for 1½ hours, and concentrated. The residue was diluted with water and neutralised with sodium bicarbonate. The aqueous phase was extracted with ethyl acetate (×2) and the combined extracts were washed with brine, dried and concentrated to give 2-acetyl-4-ethoxypyrimidine (1.8 g, 78% yield) as a colourless oil which partially solidified on standing, and was used without further purification; IR maximum (film): 1717cm$^{-1}$; $^1$H NMR (270 MHz): δ1.45(3H,t), 2.74(3H,s), 4.53(2H,q), 6.85(1H,d), 8.60(1H,d) ppm.

A solution of 2-acetyl-4-ethoxypyrimidine (1.8 g), hydroxylamine hydrochloride (0.83 g) and sodium acetate (2.2 g) in a mixture of ethanol:water (30:10 ml) was heated under reflux for 3 hours. The reaction mixture was then poured into water and extracted with ethyl acetate (×3). the combined extracts were washed with brine, dried and concentrated to give a solid which was washed with hexane to give (E)-2-acetyl-4-ethoxypyrimidine oxime as an off-white solid (1.15 g, 60% yield); $^1$H NMR (270 MHz): δ1.44(3H,t), 2.38(3H,s), 4.50(2H,q), 6.68(1H,d), 8.48(1H,d), 9.80(1H,brs) ppm.

A solution of 2-acetyl-4-ethoxy-pyrimidine oxime (0.8 g) in DMF (15 ml) was added dropwise to a stirred suspension of sodium hydride (0.10 g) in DMF (10 ml). An hour later, the reaction mixture was cooled to 0° C. and a solution of (E)-methyl 2-[2-(bromomethyl)-phenyl]-3-methoxypropenoate (1.22 g) in DMF (15 ml) was added dropwise. After a further 2 hours the mixture was poured into water and extracted with ether (×3). The organic extracts were washed with brine, dried, concentrated and chromatographed using ethyl acetate:hexane 3:2 as the eluant to give the title compound (0.84 g, 51% yield) as a white solid, m.p. 87°-89° C.; IR maxima (nujol mull): 1698, 1623 cm$^1$; $^1$H NMR (270 MHz): δ1.42(3H, t), 2.33(3H,s), 3.68(3H,s), 3.82(3H,s), 4.46(2H,q), 5.30(2H,s), 6.65(1H,d), 7.18(1H,m), 7.34(2H,m), 7.55(1H,d), 7.58(1H,s), 8.50(1H,d) ppm.

The 2-acetyl-4-ethoxypyrimidine used in this example has also been prepared as follows.

A solution of 2-chloro-4-ethoxy pyrimidine (20 g from the reaction of 1 equivalent of sodium ethoxide with 2,4-dichloropyrimidine at 0°-5° C.) in ether (50 ml) was added to ice cooled trimethylamine (50 ml of a 30% aqueous solution). After stirring the mixture for 2 hours a solution of potassium cyanide (9.0 g) in water (50 ml) was added and the resulting mixture was stirred vigorously at room temperature. After 16 hours the reaction mixture was extracted with ether (3×50 ml) and the combined extracts were washed with brine, dried and concentrated to give 2-cyano-4-ethoxypyrimidine (14.6 g, 77% yield) as a pale yellow liquid which gradually crystallised (m.p. 35° C.); $^1$H NMR (270 MHz): δ1.42(3H,t), 4.49(2H,q), 6.89(1H,d), 8.49(1H,d) ppm.

Methyl magnesium bromide (4.4 ml of a 3M solution in ether) was added to a solution of 2-cyano-4-ethoxypyrimidine in THF (20 ml) at −50° C. After 1 hour the reaction mixture was quenched by adding hydrochloric acid (10 ml of a 2M solution) followed by sodium bicarbonate to produce a neutral solution. This mixture was extracted with ether (×3) and the combined extracts were washed with water, dried and concentrated to give a dark gum, bulb to bulb distillation of this gum gave 2-acetyl-4-ethoxypyrimidine (1.35 g, 64% yield) as a white low melting solid (b.p. 70°-80° C. at 0.1 mmHg).

EXAMPLE 3

This Example illustrates the preparation of (E),(E)-methyl 2-[2-(4-[2,2,2-trifluoroethoxy]-pyrimidin-2-yl-acetoximino-methyl)phenyl]-3-methoxypropenoate (Compound No 25 of Table I).

2,2,2-Trifluoroethanol (51.3 ml) in DMF (135 ml) was added to a suspension of sodium hydride (29.5 g) in DMF (335 ml) keeping the temperature below 10° C. After 1 hour the resulting mixture was added to a solution of 2,4-dichloropyrimidine (100 g) in DMF (330 ml) keeping the temperature between −5° and −10° C. 1 Hour later the resulting reaction mixture was poured into water (1 l) and extracted with ethyl acetate (3×400 ml). The combined extracts were washed with brine, dried and concentrated to give 70% pure 2-chloro-4-(2,2,2-trifluoroethoxy)-pyrimidine (142 g) as a pale orange oil; $^1$H NMR (270 MHz): δ4.78(2H,q), 6.83(1H,d), 8.42(1H,d) ppm.

The 2-chloro-4-(2,2,2-trifluoroethoxy)-pyrimidine (142 g) in toluene (330 ml) was added to trimethylamine (140 ml of a 45% aqueous solution) at 0° C. After stirring for 16 hours the organic phase was separated off. The aqueous phase was added to toluene (330 ml) then a solution potassium cyanide (44 g in 170 ml water) was added at 0° C. The reaction mixture was stirred for a further 16 hours and then the organic phase was separated, the aqueous was extracted with ether (2×200 ml) and the combined organic extracts were dried and concentrated to give 2-cyano-4-(2,2,2-trifluoroethoxy)-pyrimidine (73.5 g, 77% yield) as a yellow oil; $^1$H NMR (270 MHz): δ4.85(2H,q), 7.10(1H,d), 8.64(1H,d) ppm.

Methyl magnesium bromide (115 ml of a 3.0M solution in ether) was added to 2-cyano-4-(2,2,2-trifluoroethoxy)-pyrimidine (70.0 g) in THF (300 ml) at −40° C. After the addition it was stirred for 1½ hours at −40° C. then treated with water (50 ml), followed by enough 2M hydrochloric acid to make the reaction mixture just acid, this was stirred for 1½ hours and then neutralised with sodium bicarbonate, and extracted with ether (3×300 ml). The combined ether extracts were dried and concentrated to give 2-acetyl-4-(2,2,2-trifluoroethoxy)-pyrimidine (66.8 g, 88% yield) as a brown oil; IR maxima (film): 1718 cm$^{-1}$; $^1$H NMR (270 MHz): δ2.74(3H,s), 4.92(2H,q), 7.05(1H,d), 8.74(1H,d) ppm.

2-Acetyl-4-(2,2,2-trifluoroethoxy)-pyrimidine (0.47 g) was dissolved in a mixture of ethanol (10 ml) and water (5 ml) and heated to 40° C. for 1 hour with hydroxylamine hydrochloride (0.16 g) and sodium acetate (0.43 g). The reaction mixture was poured into water and extracted with ethyl acetate (3×50 ml). The combined extracts were dried and concentrated. The residue was washed with hexane to give 2-acetyl-4-(2,2,2-trifluoroethoxy)-pyrimidine oxime (0.35 g, 70% yield) as a white solid, m.p. 179°–181° C.; $^1$H NMR (270 MHz): δ2.39(3H,s), 4.87(2H,q), 6.88(1H,d), 8.60(1H,d) ppm.

A solution of 2-acetyl-4-(2,2,2-trifluoroethoxy)-pyrimidine oxime (0.347 g) in DMF (5 ml) was added dropwise to a stirred suspension of sodium hydride (0.035 g) in DMF (5 ml). 1½ Hours later, the reaction mixture was cooled to 0° C. and a solution of (E)-methyl 2-[2-(bromomethyl)phenyl]-3-methoxypropenoate (0.4 g) in DMF (5 ml) was added dropwise. After 24 hours the mixture was poured in water and extracted with ethyl acetate (×3). The organic extracts were washed with brine, dried, concentrated and chromatographed using ethyl acetate:hexane 4:1 as the eluant to give the title compound (0.3 g, 49% yield) as a white solid, m.p. 90°–92° C.; IR maxima (nujol mull): 1696, 1636 cm$^{-1}$; $^1$H NMR (270 MHz): δ2.35(3H,s), 3.68(3H,s), 3.82(3H,s), 4.85(2H,q), 5.31(2H,s), 6.82(1H,d), 7.18(1H,m), 7.34(2H,m), 7.55(1H,m), 7.59(1H,s), 8.64(1H,d) ppm.

EXAMPLE 4

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. Exception to this were the test on Erysiphe graminis in which the plants were inoculated 24 hours before treatment, and in the test against Puccinia recondita for compounds Nos. 13 and 23–54, the plants were inoculated with the disease 48 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace–5% of disease on untreated plants
2 = 6–25% of disease on untreated plants
1 = 26–59% of disease on untreated plants
0 = 60–100% of disease on untreated plants The results are shown in Table III.

TABLE III

| Compound No | Table No | Pr | Egh | Egt | Sn | Po | Tc | Vi | Ca | Pv | Pil |
|---|---|---|---|---|---|---|---|---|---|---|---|
|  | I | 4 | 4 |  |  | 4 |  | 4 |  | 4 | 3 |
| 2 | I | 4 |  | 4 | 3 | 3 |  | 4 |  | 4 | 1 |
| 3 | I | 4 |  | 4 | 4 | 4 |  | 4 |  | 4 | 4 |
| 4 | I | 4 |  | 4 | 4 | 4 |  | 4 |  | 4 | 0 |
| 5 | I | 4 |  | 4 | 4 | 4 | 4 | 4 |  | 4 | 3 |
| 6 | I | 4 |  | 4 | 0 | 4 |  | 4 |  | 4 | 4 |
| 7 | I | 4$^a$ |  | 4$^a$ | 0$^a$ | 4$^a$ | 3$^a$ | 4$^a$ |  | 4$^a$ | 2$^a$ |
| 8 | I | 4 |  | 4 | 4 | 4 | 4 | 4 |  | 4 | 3 |
| 9 | I | 4 |  | 4 | 4 | 4 | 4 | 4 |  | 4 | 2 |
| 10 | I | 4 |  | 4 | 4 | 4 | 4 | 4 |  | 4 | 3 |
| 11 | I | 2 |  | 4 | 4 | 3 | 4 | — |  | 4 | — |
| 12 | I | 4$^a$ |  | 4$^a$ | 4$^a$ | 4$^a$ | 1$^a$ | 4$^a$ |  | 4$^a$ | 0$^a$ |
| 13 | I | 4 |  | 4 | 4 | 4 | 4 | 4 |  | 4 | 2 |
| 14 | I |  |  | 4 | 3 | 4 | 4 | 4 |  | 4 | 4 |
| 15 | I | 4 |  | 4 | 4 | 4 | 4 |  |  | 4 |  |
| 16 | I |  |  | 4 | 4 | 4 | 4 | 4 |  | 4 | 4 |
| 17 | I |  |  | 4 | 4 | 4 | 4 | 4 |  | 4 | 3 |
| 18 | I | 4 |  | 4 | 4 | 4 | 4 | 4 |  | 4 | 1 |
| 19 | I | 2 |  | 4 | 4 | 2 | 4 |  |  | 4 | 0 |
| 20 | I | 4 |  | 4 | 3 | 4 | 4 | 4 |  | 4 | 0 |
| 21 | I | 0 |  | 0 | 4 | 4 | 4 | 4 |  | 4 | 4 |
| 22 | I | 4 |  | 4 | 4 | 4 | 2 | 4 |  | 4 | 1 |
| 23 | I | 4 |  | 4 | 4 | 4 | 4 | 4 |  | 4 | 4 |
| 24 | I | 4 |  | 4 | 4 | 4 | 4 | 4 |  | 4 | 4 |
| 25 | I | 4 |  | 4 | 4 | 4 | 4 | 4 |  | 4 | 4 |
| 26 | I | 4 |  |  | 4 | 4 |  | 4 |  | 4 | 4 |
| 27 | I | 4 |  | 4 | 4 | 4 | 4 | 4 |  |  |  |
| 28 | I | 4 |  | 4 | 4 | 4 | 4 | 4 |  |  |  |
| 29 | I | 4 |  | 4 | 4 | 4 | 4 | 4 |  | 4 | 4 |
| 30 | I | 4 |  | 4 | 4 | 4 | 4 | 4 |  | 4 | 4 |
| 31 | I | 4 |  | 4 | 4 | 4 | 4 | 4 |  | 4 | 4 |
| 32 | I | 4 |  | 4 | 4 | 4 |  | 4 |  | 4 | 0 |
| 33 | I | 4 |  | 4 | 4 | 2 |  | 4 |  | 4 | 4 |
| 34 | I | 4 |  | 4 | 4 | 3 |  | 4 |  | 4 | 4 |
| 35 | I | 4 |  | 4 | 4 | 4 | 4 | 4 |  | 4 | 4 |
| 36 | I | 2 |  | 3 | 1 | 2 | 3 | 4 |  | — | 0 |

TABLE III-continued

| Compound No | Table No | Pr | Egh | Egt | Sn | Po | Tc | Vi | Ca | Pv | Pil |
|---|---|---|---|---|---|---|---|---|---|---|---|
| 37 | I | 4 | 4 | 4 | 4 | 4 | 4 | 4 | — | 4 | |
| 38 | I | 4 | 4 | 4 | 4 | 4 | 4 | 4 | — | 4 | |
| 39 | I | 4 | 4 | 4 | 4 | 4 | 4 | 4 | — | 1 | |
| 40 | I | 4 | 4 | 4 | 4 | 4 | 4 | 4 | — | 4 | |
| 41 | I | 4 | 4 | 4 | 4 | 4 | 4 | 0 | — | 0 | |
| 42 | I | 4 | 4 | 4 | 4 | 4 | 4 | 4 | 4 | 4 | |
| 43 | I | 4 | 4 | 4 | — | 4 | 4 | 4 | 1 | | |
| 44 | I | 4 | 4 | 4 | 4 | 4 | 4 | 4 | 4 | | |
| 45 | I | 4 | 4 | 4 | 0 | 4 | 4 | 4 | 4 | | |
| 46 | I | 4 | 4 | 4 | 4 | 4 | 4 | 4 | 4 | | |
| 47 | I | 1 | 4 | 4 | 1 | 4 | — | 4 | — | | |
| 48 | I | 4 | 4 | 4 | 4 | 4 | 4 | 4 | 4 | | |
| 50 | I | 4 | 4 | 4 | 4 | 4 | 4 | 4 | 4 | | | a = 10 ppm foliar spray only
Key to Diseases
Pr *Puccinis recondita*
Tc *Thanetophorus cucumeris*
Egh *Erysiphe graminis hordei*
Vi *Venturia inaequalis*
Egt *Erysiphe graminis tritici*
Ca *Cercospora arachidicola*
Sn *Septoria nodorum*
Pv *Plasmopara viticola*
Po *Pyricularia oryzae*
Pil *Phytophthora infestans lycopersici*

CHEMICAL FORMULAE
(as in description)

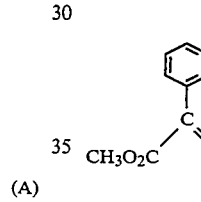

(A)

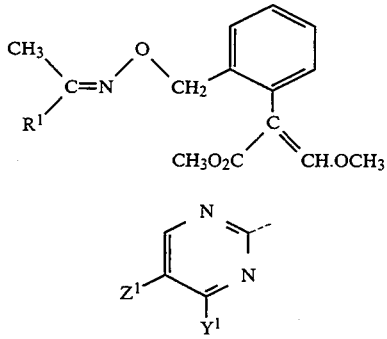

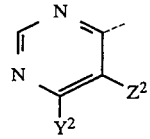

(B)

Scheme 1

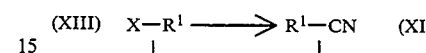

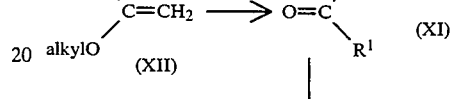

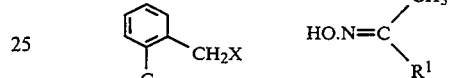

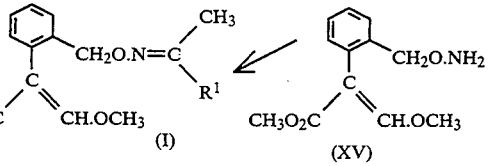

Scheme 2

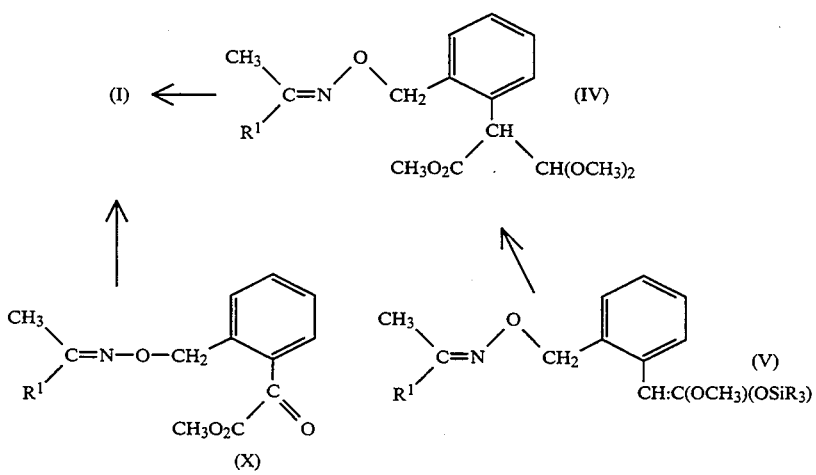

-continued

Scheme 2

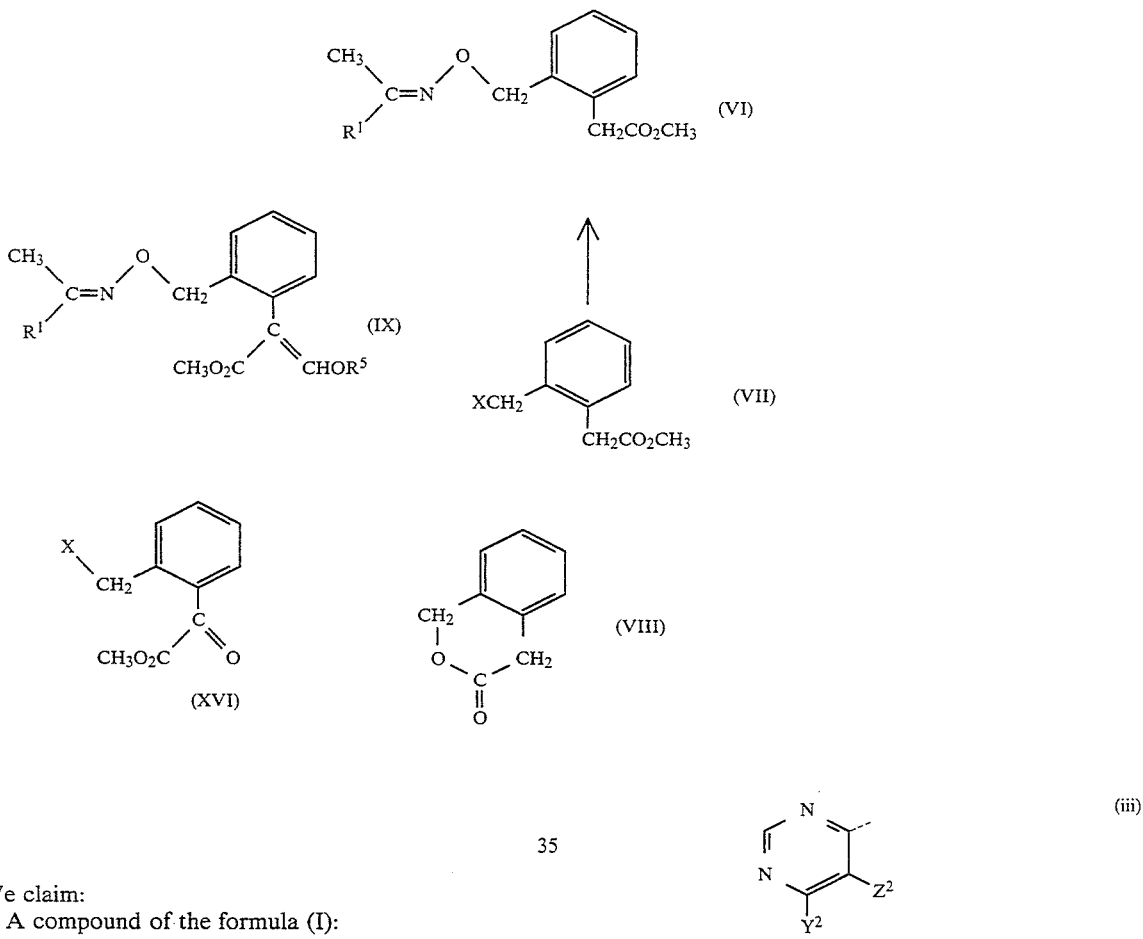

We claim:
1. A compound of the formula (I):

(I)

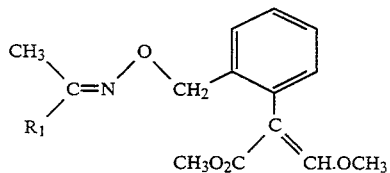

wherein $R^1$ is:
(i) pyrid-2-yl substituted by one or more groups selected from $C_{1-6}$ alkoxy, $C_{1-6}$ haloalkyl, $C_{1-6}$ haloalkoxy, $C_{1-4}$ alkoxy($C_{1-6}$)alkyl or $C_{1-4}$ alkoxy($C_{1-6}$)alkoxy;

(ii)

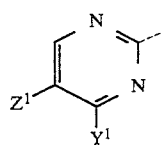

wherein $Y^1$ is $C_{2-6}$ alkyl, $C_{1-6}$ haloalkyl, $C_{1-6}$ alkoxy, $C_{1-6}$ alkylthio, $C_{1-6}$ alkylsulphinyl, $C_{1-6}$ haloalkoxy, $C_{1-6}$ alkoxy($C_{1-6}$)alkyl, $C_{1-6}$ alkoxy($C_{1-6}$)alkoxy, $C_{1-4}$ alkoxy($C_{1-6}$)alkoxy($C_{1-6}$)alkoxy, di($C_{1-4}$ alkoxy)($C_{1-6}$)alkoxy, $C_{2-6}$ alkenyloxy or $C_{2-6}$ alkynyloxy and $Z^1$ is hydrogen, fluorine, chlorine or $C_{1-6}$ alkyl; or $Y^1$ is methyl and $Z^1$ is fluorine, chlorine or $C_{1-6}$ alkyl; or, (iii)

wherein $Y^2$ is $C_{2-6}$ alkyl, $C_{1-6}$ haloalkyl, $C_{2-6}$ alkoxy, $C_{1-6}$ alkylthio, $C_{1-6}$ alkylsulphinyl, $C_{1-6}$ haloalkoxy or $C_{2-4}$ alkynyloxy and $Z^2$ is hydrogen, fluorine, chlorine or $C_{1-4}$ alkyl; or $Y^2$ is methyl or methoxy and $Z^2$ is fluorine, chlorine or $C_{1-4}$ alkyl.

2. A compound as claimed in claim 1 wherein $Y^1$ is $C_{2-6}$ alkyl, $C_{1-6}$ haloalkyl, $C_{1-6}$ alkoxy, $C_{1-6}$ alkylthio, $C_{1-6}$ alkylsulphinyl, $C_{1-6}$ haloalkoxy or $C_{2-4}$ alkynyloxy and $Z^1$ is hydrogen, fluorine, chlorine or $C_{1-4}$ alkyl; or $Y^1$ is methyl and $Z^1$ is fluorine, chlorine or $C_{1-4}$ alkyl.

3. A compound as claimed in claim 1 wherein $Y^1$ is $C_{2-6}$ alkoxy or $C_{1-6}$ haloalkoxy and $Z^1$ is hydrogen, chlorine, fluorine or methyl.

4. A compound as claimed in claim 1 wherein $Y^2$ is $C_{2-6}$ alkoxy or $C_{1-6}$ haloalkoxy and $Z^2$ is hydrogen, chlorine, fluorine or methyl.

5. A compound as claimed in claim 1 wherein $R^1$ is 6-trifluoromethylpyrid-2-yl (compound No. 2), 4-trifluoromethylpyrid-2-yl (compound No. 4), 4-trifluoromethylpyrimidin-2-yl (compound No. 5), 4-ethoxypyrimidin-2-yl (compound No. 6), 4-methoxypyrid-2-yl (compound No. 8), 4-methylthiopyrimidin-2-yl (compound No. 9), 4-methoxypyrimidin-2-yl (compound No. 10), 4-propargyloxypyrimidin-2-yl (compound No. 11), 4-n-propyloxypyrimidin-2-yl (compound No. 12), 4-n-butyloxypyrimidin-2-yl (compound No. 13), 3-trifluoromethylpyrid-2-yl (compound No. 14), 4-iso-propyloxypyrimidin-2-yl (compound No. 15), 4-ethoxypyrid-2-yl (compound No. 16), 4-ethylthiopyrimidin-2-yl (compound No. 17), 3-methoxypyrid-2-yl (compound No. 18), 3-ethoxypyrid-2-yl (compound No; 19), 6-methoxypyrid-2-yl (compound No. 20), 6-ethylpyrimidin-4-yl (compound No. 21), 4-ethoxy-5-methylpyrimidin-2-yl (compound No. 22), 4-iso-propyloxypyrid-2-yl (compound No. 23), 6-iso-propyloxypyrimidin-4-yl (compound No. 24), 4-(2,2,2-trifluoroethoxy)pyrimidin-2-yl (compound No. 25), 4-methoxyethoxypyrid-2-yl (compound No. 27), 4-methoxy-5-methylpyrimidin-2-yl (compound No. 28), 5-trifluoromethylpyrid-2-yl (compound No. 29), 4-iso-propyloxy-5-methyl-pyrimidin-2-yl (compound No. 30), 4-(2,2,2-trifluoroethoxy)-5-methylpyrimidin-2-yl (compound No. 31), 6-ethoxypyrid-2-yl (compound No. 32), 4-ethoxy-5-fluoropyrimidin-2-yl (compound No. 33), 4-methoxy-5-fluoropyrimidin-2-yl (compound No. 34) 6-(2,2,2-trifluoroethoxy)pyrimidin-4-yl (compound No. 35), 4-trifluoromethyl-6-(2,2,2-trifluoroethoxy)pyrid-2-yl (compound No. 36), 4-(2,2,2-trifluoroethoxy)-5-fluoropyrimidin-2-yl (compound No. 37), 4-iso-propyloxy-5-fluoropyrimidin-2-yl (compound No. 38), 4-trifluoromethyl-6-ethoxypyrid-2-yl (compound No. 39), 4-(2,2,3,3-tetrafluoro-n-propyloxy)pyrimdin-2-yl (compound No. 40), 4-trifluoromethyl-6-methoxypyrid-2-yl (compound No. 41), 4-(2,2,2-trifluoroethoxy)pyrid-2-yl (compound No. 42) or 5-iso-propyl-6-methoxypyrimidin-4-yl (compound No. 43).

6. The intermediate compound 2-acetyl-4-(2,2,2-trifluoroethoxy)pyrimidine.

7. A fungicidal composition comprising, as an active ingredient, a compound as claimed in claim 1 and a fungicidally acceptable carrier of diluent therefor.

8. A process for combating fungi which comprises applying to a plant, to a seed of a plant or to the locus thereof, a fungicidally effective amount of a compound as claimed in claim 1.

* * * * *